US005631404A

United States Patent [19]

Anzai et al.

[11] Patent Number: 5,631,404

[45] Date of Patent: May 20, 1997

[54] DIAMINE COMPOUNDS FOR USE IN ELECTROPHOTOGRAPHIC PHOTOCONDUCTORS

[75] Inventors: Mitsutoshi Anzai; Yasuo Murakami; Atsushi Takesue, all of Tokyo; Masaomi Sasaki, Susono; Tomoyuki Shimada, Shizuoka-ken; Tamotsu Aruga, Mishima; Masafumi Ohta, Susono, all of Japan

[73] Assignees: Ricoh Company, Ltd.; Hodogaya Chemical Co., Ltd., both of Tokyo, Japan

[21] Appl. No.: 457,237

[22] Filed: Jun. 1, 1995

Related U.S. Application Data

[62] Division of Ser. No. 326,224, Oct. 20, 1994, Pat. No. 5,489,495.

[30] Foreign Application Priority Data

| | | | |
|---|---|---|---|
| Oct. 20, 1993 | [JP] | Japan | 5-285857 |
| Nov. 1, 1993 | [JP] | Japan | 5-296045 |
| Apr. 25, 1994 | [JP] | Japan | 6-109087 |
| Apr. 25, 1994 | [JP] | Japan | 6-109088 |

[51] Int. Cl.$^6$ .......... C07C 211/01

[52] U.S. Cl. .......... 564/308; 564/322; 564/330; 564/426; 564/427; 564/429

[58] Field of Search .......... 564/308, 322, 564/330, 426, 427, 429

[56] References Cited

U.S. PATENT DOCUMENTS

| | | | |
|---|---|---|---|
| 5,312,707 | 5/1994 | Ota et al. | 430/59 |
| 5,475,137 | 12/1995 | Shimada et al. | 564/308 |

FOREIGN PATENT DOCUMENTS

| | | |
|---|---|---|
| 4-186362 | 7/1992 | Japan . |

*Primary Examiner*—Richard L. Raymond
*Attorney, Agent, or Firm*—Oblon, Spivak, McClelland, Maier & Neustadt, P.C.

[57] ABSTRACT

An electrophotographic photoconductor includes an electroconductive support and a photoconductive layer formed thereon containing a diamine compound represented by formula (I):

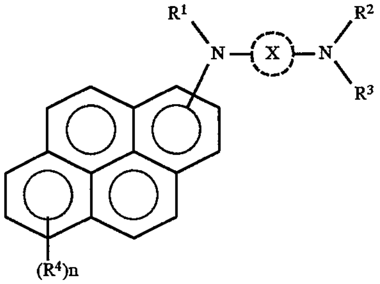

(I)

wherein $R^1$, $R^2$, and $R^3$ each is independently a substituted or unsubstituted alkyl group or aryl group; $R^4$ is hydrogen, an alkyl group or an alkoxyl group; n is an integer of 1 to 3; and

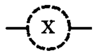

is a substituted or unsubstituted bivalent arylene group or a bivalent heterocyclic group. This diamine compound is useful as a photoconductive material for electrophotographic photoconductors.

21 Claims, 3 Drawing Sheets

DIAMINE COMPOUNDS FOR USE IN ELECTROPHOTOGRAPHIC PHOTOCONDUCTORS

This is a Division of application Ser. No. 08/326,224 filed on Oct. 20, 1994, now U.S. Pat. No. 5,489,495.

BACKGROUND OF THE INVENTION

1. Field of the Invention

The present invention relates to an electrophotographic photoconductor, and more particularly an electrophotographic photoconductor comprising an electroconductive support and a photoconductive layer comprising an diamine compound as an organic photoconductive material, which is formed on the electroconductive support. The present invention also relates to diamine compounds for use as organic photoconductive materials for the electrophotographic photoconductor.

2. Discussion of Background

Conventionally, inorganic materials such as selenium, cadmium sulfide and zinc oxide are used as a photoconductive material of an electrophotographic photoconductor in an electrophotographic process. The electrophotographic process is an image formation processes, through which the surface of a photoconductor is charged uniformly in the dark to a predetermined polarity, for instance, by corona charge. The uniformly charged photoconductor is exposed to a light image to selectively dissipate the electrical charges of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor for in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; a photoconductor comprising an amine derivative as a charge transporting material, as described in Japanese Laid-Open Patent Application 57-195254; a photoconductor comprising poly-N-vinylcarbazole and an amine derivative as charge transporting materials, as described in Japanese Laid-Open Patent Application 58-1155; and a photoconductor comprising a polyfunctional tertiary amine compound, in particular benzidine compound, as a photoconductive material, as described in U.S. Pat. No. 3,265,496, Japanese Patent Publication 39-11546 and Japanese Laid-Open Patent Application 53-27033.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to provide an electrophotographic photoconductor free from the conventional shortcomings, which can completely satisfy all the requirements in the electrophotographic process, including excellent flexibility.

A second object of the present invention is to provide a photoconductive material for use in the above-mentioned electrophotographic photoconductor.

The first object of the present invention can be achieved by an electrophotographic photoconductor comprising an electroconductive support and a photoconductive layer formed thereon comprising as an effective component at least a diamine compound of formula (I):

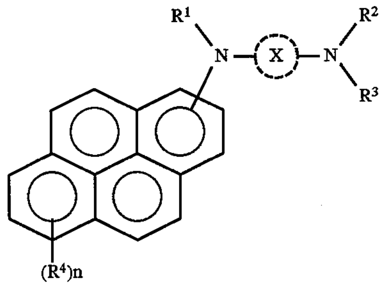

(I)

wherein $R^1$, $R^2$, and $R^3$ each is independently a substituted or unsubstituted alkyl group or aryl group; $R^4$ is hydrogen, an alkyl group or an alkoxyl group; n is an integer of 1 to 3; and

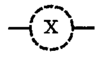

is a substituted or unsubstituted bivalent arylene group or a bivalent heterocyclic group.

The second object of the present invention can be achieved by a diamine compound of the above formula (I).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
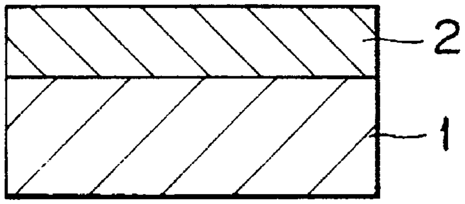
FIG. 1 is a schematic cross-sectional view of a first example of an electrophotographic photoconductor according to the present invention.

The diamine compound for use in the electrophotographic photoconductor according to the present invention is a diamine compound with the following formula (I):

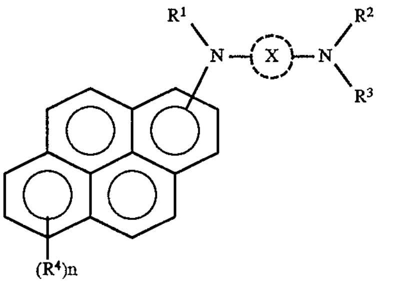

(I)

wherein $R^1$, $R^2$, and $R^3$ each is independently a substituted or unsubstituted alkyl group or aryl group; $R^4$ is hydrogen, an alkyl group or an alkoxyl group; n is an integer of 1 to 3; and

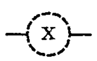

is a substituted or unsubstituted bivalent arylene group or a bivalent heterocyclic group.

The above compound is a novel compound and can be synthesized by the combination of (a) an N-alkyl substitution reaction or N-aryl substitution reaction of an amino compound corresponding to the diamine compound and (b) an N-pyrenyl substitution reaction. For the alkylation, arylation and pyrenyl condensation, corresponding halides are generally employed, and for diaryl condensation, Ullmann reaction is generally employed. In the Ullmann reaction, a solvent, for instance, N-dimethylformamide, nitrobenzene, dimethylsulfoxide, and dichlorobenzene can be employed. As a basic compound serving as an agent for removing HZ (wherein Z is a halogen atom) produced in the course of the Ullmann reaction, for instance, potassium carbonate, sodium carbonate, sodium hydrogencarbonate can be employed. The reaction temperature is usually in a range of 160° to 250° C.

When the reactivities of employed components for the Ullmann reaction are low, the reaction may be carried out at elevated temperatures in an autoclave or the like. Catalysts such as copper powder, copper oxide and halogenated copper are usually used for promoting the reaction.

In the formula (I) of the diamine compound, when $R^1$, $R^2$ and/or $R^3$ is an aryl group, specific examples of such an aryl group include a non-fused hydrocarbon group such as phenyl group, biphenylyl group, and terphenylyl group, and a fused polycyclic hydrocarbon group.

It is preferable that the fused polycyclic hydrocarbon group be such that the number of carbon atoms which form rings be 18 or less. Specific examples of such a fused polycyclic hydrocarbon group include pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrenyl group, aceanthrenyl group, triphenylenyl group, pyrenyl group, chrysenyl group, and naphthacenyl group.

Furthermore, when

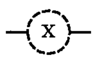

in formula (I) is an arylene group, specific examples of such an arylene group include a bivalent group of a monocyclic hydrocarbon compound such as benzene, diphenyl ether, polyethylene glycol diphenyl ether, diphenylthio ether, and diphenylsulfone; a bivalent group of a non-fused polycyclic hydrocarbon compound such as biphenyl, polyphenyl, diphenyl alkane, diphenyl alkene, diphenyl alkyne, triphenyl methane, distyrylbenzene, 1,1-diphenylcyclo alkane, polyphenyl alkane, and polyphenyl alkene; bivalent groups of fused polycyclic hydrocarbons previously mentioned as specific examples of $R^1$; and bivalent groups of hydrocarbon ring assemblies such as 9,9-diphenylfluorenone.

When

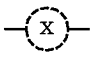

in formula (I) is a bivalent heterocyclic group, specific examples of such a bivalent heterocyclic group include bivalent groups of carbazole, dibenzofuran, dibenzothiophene, oxadiazole, and thiadiazole.

When $R^1$, $R^2$ and/or $R^3$ is an aryl group, and

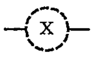

is a bivalent group of an arylene group or heterocyclic group, the aryl group or the bivalent group may have any of the following substituents:

(1) A halogen atom, cyano group, and nitro group.

(2) An alkyl group, preferably a straight chain or branched alkyl group having 1 to 12 carbon atom, more preferably having 1 to 8 carbon atoms, furthermore preferably having 1 to 4 carbon atoms. These alkyl groups may have a substituent such as a fluorine atom, a hydroxyl group, a cyano group, an alkoxyl group having 1 to 4 carbon atoms, or a phenyl group which may have a substituent such as a halogen atom, an alkyl group having 1 to 4 carbon atoms, or an alkoxyl group having 1 to 4 carbon atoms. Specific examples of such an alkyl group are methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxy-benzyl group, and 4-phenylbenzyl group.

(3) An alkoxyl group (—$OR^5$) in which $R^5$ is the same alkyl group as above defined in (2). Specific examples of such an alkoxyl group are methoxy group, ethoxy group, n-propoxy group, i-propoxy group, t-butoxy group, n-butoxy group, s-butoxy group, i-butoxy group, 2-hydroxyethoxy group, 2-cyano-ethoxy group, benzyloxy group, 4-methylbenzyloxy group, and trifluoromethoxy group.

(4) An aryloxy group. Examples of the aryl group in the aryloxy group are phenyl group and naphthyl group. The aryloxy group may have a substituent such as an alkoxyl group having 1 to 4 carbon atoms, an alkyl group having 1 to 4 carbon atoms, or a halogen atom. Specific examples of the aryloxy group are phenoxy group, 1-naphthyloxy group, 2-naphthyloxy group, 4-methylphenoxy group, 4-methoxyphenoxy group, 4-chlorophenoxy group, and 6-methyl-2-naphthyloxy group.

(5) An alkylmercapto group or an arylmercapto group. Specific examples of the alkylmercapto or arylmercapto group are methylthio group, ethylthio group, phenylthio group, and p-methylphenylthio group.

(6) 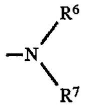

in which $R^6$ and $R^7$ each is hydrogen, the alkyl group as defined in (2), or an aryl group. Specific examples of the aryl group are phenyl group, biphenylyl group, and naphthyl group, which may have a substituent such as an alkoxyl group having 1 to 4 carbon atoms, an alkyl group having 1 to 4 carbon atoms, or a halogen atom. $R^6$ and $R^7$ in combination may form a ring, or may form a ring in combination with a carbon atom in the aryl group. Specific examples of this amino or amino derivative group are amino group, diethyl amino group, N-methyl-N-phenylamino group, N,N-diphenylamino group, N,N-di(p-tolyl)amino group, benzylamino group, piperidino group, morpholino group, and julolidyl group.

(7) An alkylenedioxy or alkylenedithio group such as methylenedioxy group and methylenedithio group.

When any of $R^1$, $R^2$, $R^3$ and $R^4$ is an alkyl group, specific examples of the alkyl group may be the same as provided in (2) above.

Specific examples of the diamine compound represented by formula (I) are shown in the following TABLE 1:

TABLE 1

| No. | 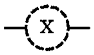 | $R^1$ | $R^2$ | $R^3$ | $(R^4)n$ | SPPR* |
|---|---|---|---|---|---|---|
| 1 | 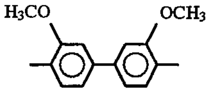 | 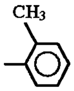 | 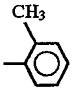 | 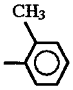 | H | 1- |
| 2 | " | 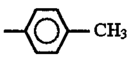 | 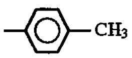 | 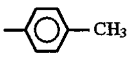 | H | 1- |
| 3 | " | 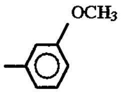 | 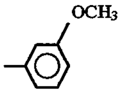 | 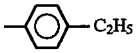 | H | 1- |
| 4 | " | 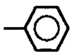 | 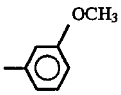 | 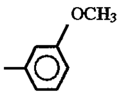 | H | 1- |
| 5 | 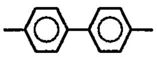 | 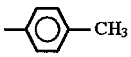 | 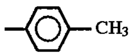 | 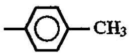 | H | 1- |
| 6 | " | 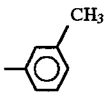 | 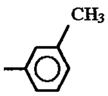 | 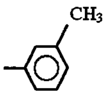 | H | 1- |
| 7 | " | 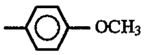 | 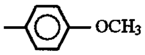 | 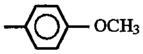 | H | 1- |
| 8 | " | 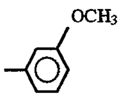 | 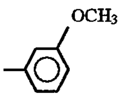 | 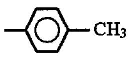 | H | 1- |
| 9 | " | 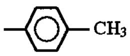 | 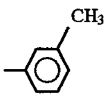 | 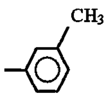 | H | 1- |

TABLE 1-continued
| No. | 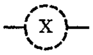 | $R^1$ | $R^2$ | $R^3$ | $(R^4)n$ | SPPR* |
|---|---|---|---|---|---|---|
| 10 | " | 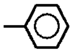 | 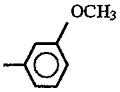 | 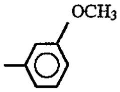 | H | 1- |
| 11 | " | 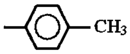 | 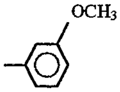 | 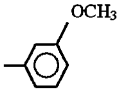 | H | 1- |
| 12 | " | 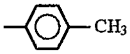 | 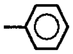 | 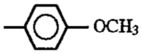 | H | 1- |
| 13 | 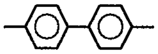 | $-C_2H_5$ | $-C_2H_5$ | $-C_2H_5$ | H | 1- |
| 14 | " | 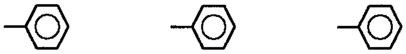 | | | 7-t-Bu | 1- |
| 15 | " | 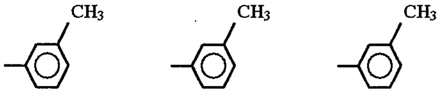 | | | H | 4- |
| 16 | " | 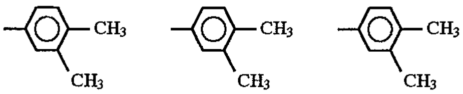 | | | H | 1- |
| 17 | " | 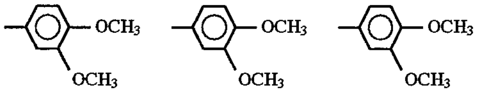 | | | H | 1- |
| 18 | " | 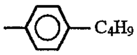 | 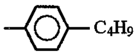 | 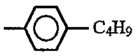 | H | 1- |
| 19 | " | 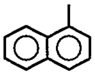 | 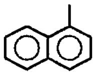 | 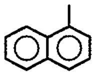 | H | 1- |
| 20 | " | $C_2H_5$ | $C_4H_9$ | $C_4H_9$ | H | 1- |
| 21 | " | $-C_2H_5$ | $-C_2H_5$ | 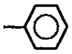 | H | 1- |
| 22 | " | 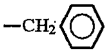 | 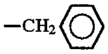 | 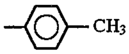 | H | 1- |
| 23 | " | 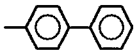 | 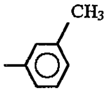 | 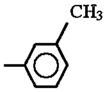 | H | 1- |
| 24 | " | pyrenyl (1-) | pyrenyl (1-) | pyrenyl (1-) | H | 1- |
| 25 | 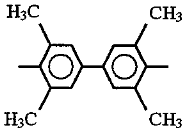 | 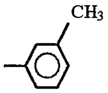 | 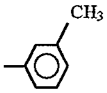 | 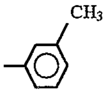 | H | 1- |
| 26 | " | 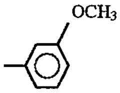 | 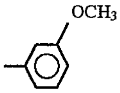 | 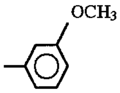 | H | 1- |

TABLE 1-continued
| No. | 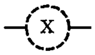 | R¹ | R² | R³ | (R⁴)n | SPPR* |
|---|---|---|---|---|---|---|
| 27 | 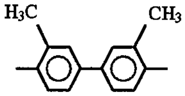 | 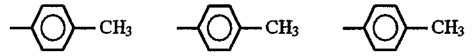 | | | H | 1- |
| 28 | " | 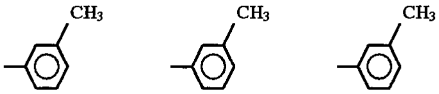 | | | H | 1- |
| 29 | " | 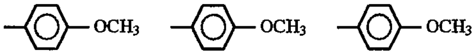 | | | H | 1- |
| 30 | " | 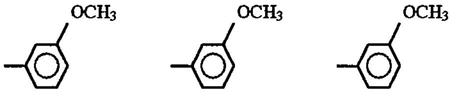 | | | H | 1- |
| 31 | " | pyrenyl (1-) | 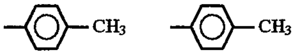 | | H | 1- |
| 32 | " | 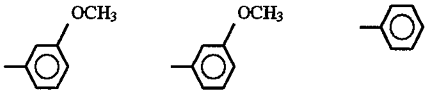 | | | H | 1- |
| 33 | " | $C_2H_5$ | $C_2H_5$ | 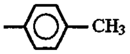 | H | 1- |
| 34 | 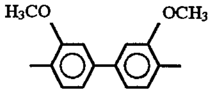 | 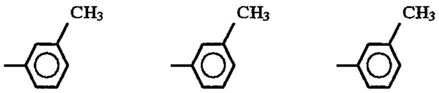 | | | H | 1- |
| 35 | 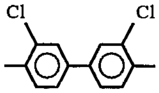 | 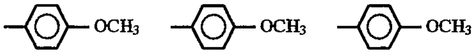 | | | H | 1- |
| 36 | 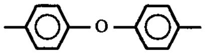 | 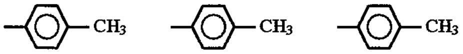 | | | H | 1- |
| 37 | " | 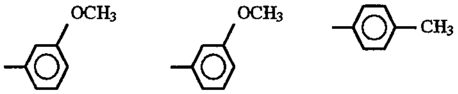 | | | H | 1- |
| 38 | 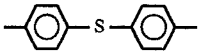 | 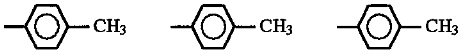 | | | H | 1- |
| 39 | 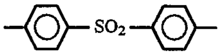 | 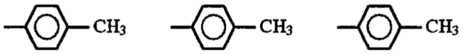 | | | H | 1- |
| 40 | 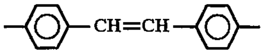 | 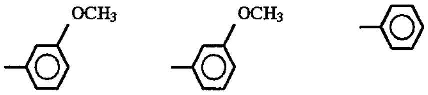 | | | H | 1- |
| 41 | 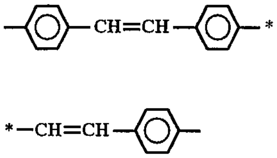 | 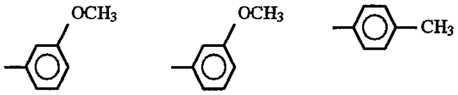 | | | H | 1- |
| 42 | 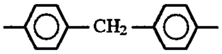 | 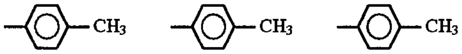 | | | H | 1- |
| 43 | " | 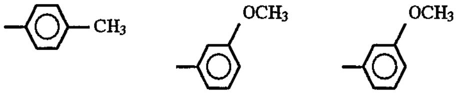 | | | H | 1- |

TABLE 1-continued
| No. | 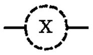 | R[1] | R[2] | R[3] | (R[4])n | SPPR* |
|---|---|---|---|---|---|---|
| 44 | " | 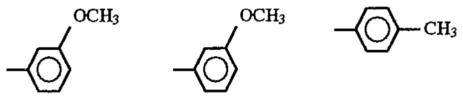 | | | H | 1- |
| 45 | 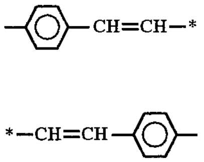 | 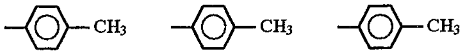 | | | H | 1- |
| 46 | 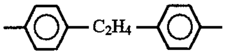 | 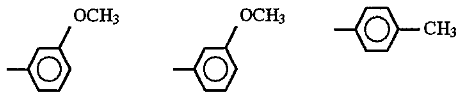 | | | H | 1- |
| 47 | 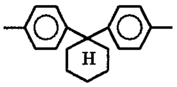 | 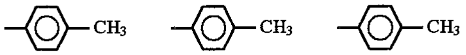 | | | H | 1- |
| 48 | 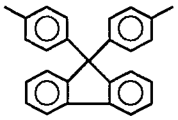 | 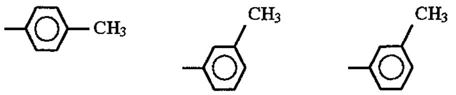 | | | H | 1- |
| 49 | 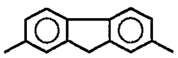 | 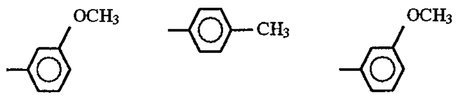 | | | H | 1- |
| 50 | 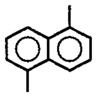 | 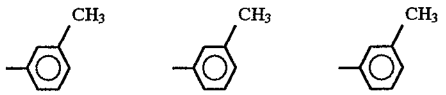 | | | H | 1- |
| 51 | 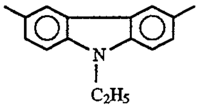 | 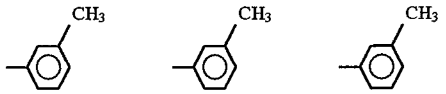 | | | H | 1- |
| 52 | 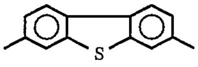 | 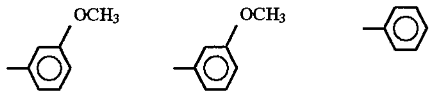 | | | H | 1- |
| 53 | 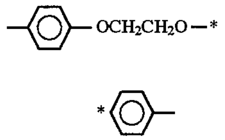 | 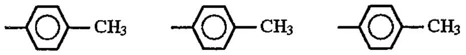 | | | H | 1- |
| 54 | " | 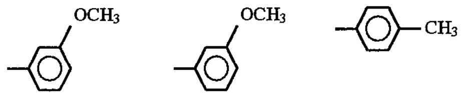 | | | H | 1- |
| 55 | " | 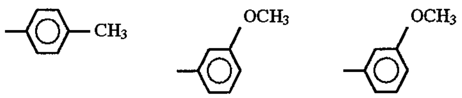 | | | H | 1- |
| 56 | 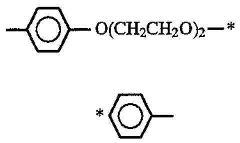 | 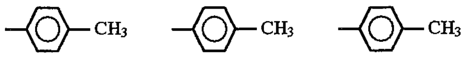 | | | H | 1- |

TABLE 1-continued

| No. | 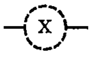 | $R^1$ | $R^2$ | $R^3$ | $(R^4)n$ | SPPR* |
|---|---|---|---|---|---|---|
| 57 | " | 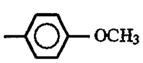 | 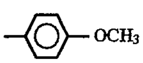 | 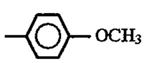 | H | 1- |
| 58 | " | 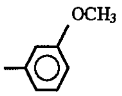 | 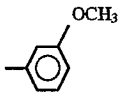 | 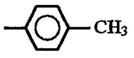 | H | 1- |
| 59 | " | 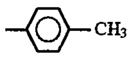 | 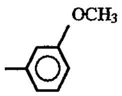 | 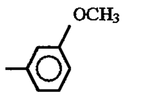 | H | 1- |
| 60 | 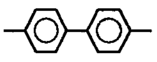 | 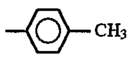 | 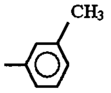 | 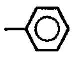 | H | 1- |
| 61 | 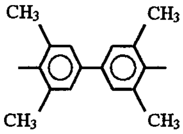 | 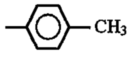 | 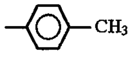 | 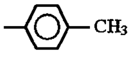 | H | 1- |

Note) SPPR*: Substitution Position of Pyrene Ring

Of the diamine compounds covered by the above-mentioned formula (I), a diamine compound of the following formula (Ia) may also be particularly useful as a photoconductive material for use in the electrophotographic photoconductor according to the present invention:

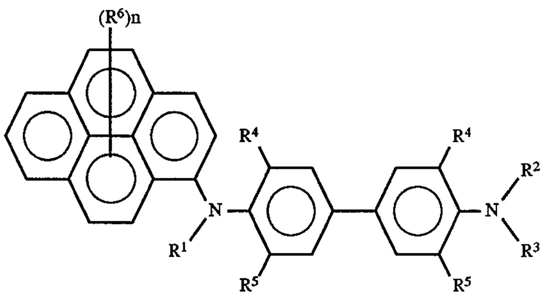

(Ia)

wherein $R^1$, $R^2$ and $R^3$ each is independently a substituted or unsubstituted alkyl group or aryl group; $R^4$ is hydrogen, a halogen atom, methoxy group or methyl group; $R^5$ is hydrogen or methyl group; $R^6$ is hydrogen, an alkyl group or an alkoxyl group; and n is an integer of 1 to 3.

The diamine compound of formula (Ia) can be synthesized, for example, by the following steps:

(1) The following diamine compound of formula (II) to N-acetylation is subjected to N-acetylation to obtain an N-acetylated compound of the diamine compound of formula (II):

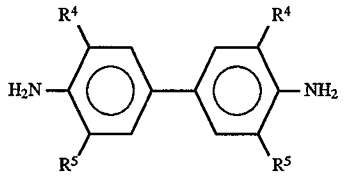

(II)

wherein $R^4$ is hydrogen, chlorine, methoxy group or methyl group; and $R^5$ is hydrogen or methyl group.

(2) The thus obtained N-acetylated compound is then subjected to an N,N',N'-three-substitution reaction by use of a halide of the following formula (III) to obtain a condensation product:

$R^1Z^1$, $R^2Z^1$ or $R^3Z^1$ (III)

wherein $R^1$, $R^2$ and $R^3$ each is independently a substituted or unsubstituted alkyl group or aryl group; and $Z^1$ is a chlorine atom, a bromine atom or an iodine atom.

(3) The thus obtained condensation product is hydrolyzed.

(4) The hydrolyzed condensation product is condensed with a pyrenyl halide of formula (IV) by the Ullmann condensation reaction, whereby the above-mentioned diamine compound of formula (Ia) can be synthesized:

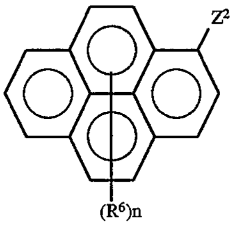

(IV)

wherein $R^6$ is hydrogen, an alkyl group, or an alkoxyl group; n is an integer of 1 to 3; and $Z^2$ is bromine or iodine.

Alternatively, a 4-iodo-4'-nitro-1,1'-biphenyl compound of formula (V) is condensed with an amine compound of formula (VI) to prepare a condensation product:

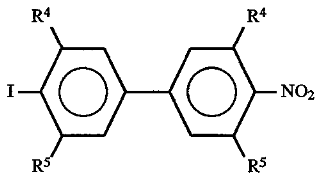

(V)

wherein $R^4$ is hydrogen, chlorine, methoxy group or methyl group; and $R^5$ is hydrogen or methyl group.

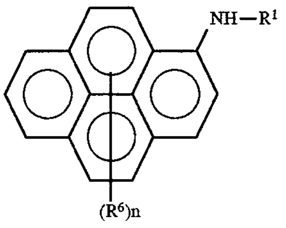

(VI)

wherein $R^1$ is a substituted or unsubstituted alkyl group or aryl group; $R^6$ is hydrogen, an alkyl group or an alkoxyl group; and n is an integer of 1 to 3.

The thus obtained condensation product is reduced and condensed with the previously mentioned halide of formula (III) by the Ullmann condensation reaction, whereby the diamine compound of formula (Ia) can be obtained.

When each of $R^1$, $R^2$, and $R^3$ of the previously mentioned formula (III) is an alkyl group, the diamine compound of formula (II) can also be used as an acid removing agent for removing HX wherein X is a halogen in the course of the reaction. Alternatively, the N,N,N'-three-substitution reaction is carried out by use of an organic amine, sodium hydrogencarbonate, potassium hydrogencarbonate, sodium carbonate or potassium carbonate, each of which has a stronger basicity than the diamine compound of formula (II), as the acid removing agent in the presence of a polar solvent such as pyridine, acetone, THF, methanol, or ethanol, or without solvent.

Examples of the thus obtained diamine compound of formula (Ia) according to the present invention are as follows:

In formula (Ia), specific examples of the alkyl group represented by $R^1$, $R^2$, or $R^3$ include methyl group, ethyl group, propyl group, butyl group and benzyl group. Specific examples of the aryl group represented by $R^1$, $R^2$, or $R^3$ include phenyl group, biphenylyl group, terphenylyl group, naphthyl group, and anthryl group. These groups may have any of the following substituents: an alkyl group such as methyl group, ethyl group, propyl group, and butyl group; an alkoxyl group such as methoxy group, ethoxy group, propoxy group, and butoxy group; an alkylmercapto group such as methylthio group and ethylthio group; an aryloxy group such as phenoxy group and naphthyloxy group; and a halogen.

When any of $R^1$, $R^2$, or $R^3$ has a plurality of substituents, such substituents may be the same or different.

Specific examples of the alkyl group represented by $R^6$ are methyl group, ethyl group and butyl group; and specific examples of the alkoxyl group represented by $R^6$ are methoxy group and ethoxy group.

Specific examples of the diamine compound of formula (II) serving as a starting material for the synthesis of the diamine compound of formula (Ia) are benzidine, 3,3'-dimethylbenzidine, 3,3'-dimethoxybenzidine, 3,3'-dichlorobenzidine, and 3,3',5,5'-tetramethylbenzidine.

The diamine compounds according to the present invention, which are remarkably effective as photoconductive materials for use in electrophotographic photoconductors, can be optically or chemically sensitized with a sensitizer such as a dye or Lewis acid. In addition, the diamine compounds effectively function as a charge transporting material in a function-separated type electrophotographic photoconductor where an organic or inorganic pigment serves as a charge generating material.

Specific examples of a sensitizing dye for use in the present invention are triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; pyrylium dyes such as 2,6-diphenyl-4-(N,N-dimethylaminophenyl) thiapyrylium perchlorate and benzopyrylium salts (described in Japanese Patent Publication 48-25658); 2,4,7-trinitro-9-fluorenone; and 2,4-dinitro-9-fluorenone. These sensitizing dyes can be used alone or in combination.

Examples of the above-mentioned organic pigments include azo pigments such as C.I. Pigment Blue 25 (C.I. 21180), C.I. Pigment Red 41 (C.I. 21200), and C.I. Pigment Red 3 (C.I. 45210); phthalocyanine pigments such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R.

Examples of the inorganic pigments are selenium, selenium—tellurium, cadmium sulfide, cadmium sulfide—selenium and α-silicone.

In the photoconductors according to the present invention, at least one diamine compound of formula (I) is contained in the photoconductive layers 2, **2*a*, 2*b*, 2*c* and 2*d*. The diamine compound can be employed in different ways, for example, as shown in FIGS. 1 through 5**.

In the photoconductor as shown in FIG. 1, a photoconductive layer 2 is formed on an electroconductive support 1, which photoconductive layer 2 comprises a diamine compound of the present invention, a sensitizing dye and a binder agent (binder resin). In this photoconductor, the diamine compound works as a photoconductive material, through which charge carriers which are necessary for the light decay of the photoconductor are generated and transported. However, the diamine compound itself scarcely absorbs light in the visible light range and, therefore, it is necessary to add a sensitizing dye which absorbs light in the visible light range in order to form latent electrostatic images by use of visible light.

Figure 2:
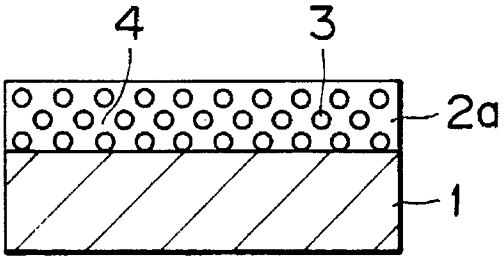
FIG. 2 as a schematic cross-sectional view of a second example of an electrophotographic photoconductor according to the present invention.

Referring to FIG. 2, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer **2*a* comprising a charge generating material 3 dispersed in a charge transporting medium 4 comprising a diamine compound and a binder agent. In this embodiment, the diamine compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3** and transports those charge carriers.

In this electrophotographic photoconductor, it is basically necessary that the light-absorption wavelength regions of the charge generating material 3 and the polyether compound not overlap in the visible light range. This is because, in order that the charge generating material 3 produce charge carriers efficiently, it is necessary that light pass through the charge transporting medium 4 and reach the surface of the charge generating material 3. Since the diamine compounds of the previously described general formula (I) do not substantially absorb light in the visible range, they can work effectively as charge transporting materials in combination with the charge generating material 3 which absorbs the light in the visible region and generates charge carriers.

Figure 3:
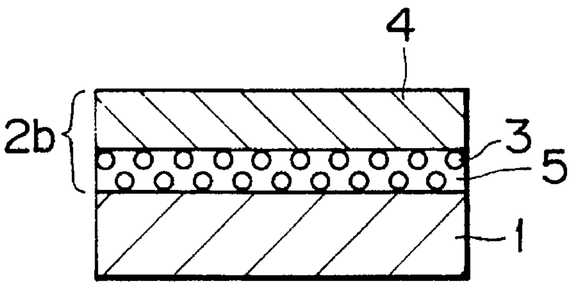
FIG. 3 as a schematic cross-sectional view of a third example of an electrophotographic photoconductor according to the present invention.

Referring to FIG. 3, there is shown an enlarged cross-sectional view of a further embodiment of an electrophotographic photoconductor according to the present invention. In the figure, there is formed on an electroconductive support 1 a two-layered photoconductive layer 2*b* comprising a charge generation layer 5 containing the charge generating material 3, and a charge transport layer 4 containing a diamine compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the polyether compound mainly works for transporting charge carriers. The generation and transportation of the charge carriers are performed by the same mechanism as that in the photoconductor shown in FIG. 2.

Figure 4:
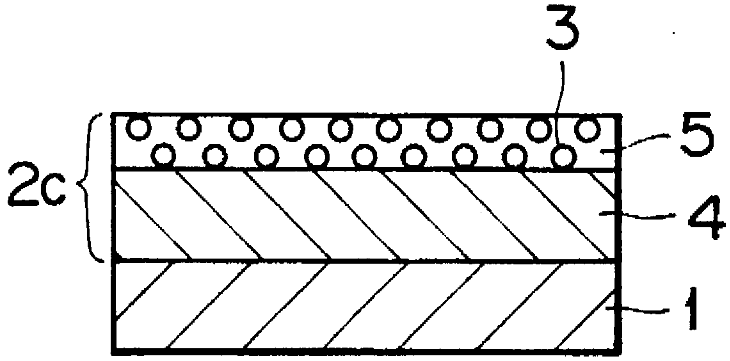
FIG. 4 as a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of the charge generation layer 5 and the charge transport layer 4 is reversed in view of the electrophotographic photoconductor as shown in FIG. 3. The mechanism of the generation and transportation of charge carriers is substantially the same as that of the photoconductor shown in FIG. 3.

Figure 5:
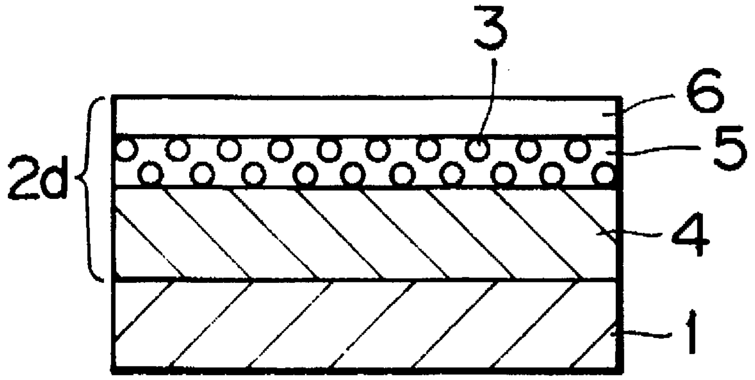
FIG. 5 is a schematic cross-sectional view of a fifth example of an electrophotographic photoconductor according to the present invention.

In the above photoconductor, a protective layer 6 may be formed on the charge generation layer 5 as shown in FIG. 5 for protecting the charge generation layer 5.

When the electrophotographic photoconductor according to the present invention as shown in FIG. 1 is prepared, at least one diamine compound of the previously described formula (I) is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the diamine compound contained in the photoconductive layer 2 be in the range or 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

The electrophotographic photoconductor shown in FIG. 2 can be obtained by dispersing finely-divided particles of the charge generating material 3 in the solution in which at least one diamine compound for use in the present invention and the binder agent are dissolved, coating the above-prepared dispersion on the electroconductive support 1 and then drying the same to form the photoconductive layer 2*a*.

It is preferable that the thickness of the photoconductive layer 2*a* be in the range of 3 to 50 μm, more preferably in the range of 5 to 20 μm. It is preferable that the amount of the diamine compound contained in the photoconductive layer 2*a* be in the range or 10 to 95 wt. %, more preferably in the range of 30 to 90 wt. %.

It is preferable that the amount of the charge generating material 3 contained in the photoconductive layer 2*a* be in the range of 0.1 to 50 wt. %, more preferably in the range of 1 to 20 wt. %.

Specific examples of the charge generating material 3 for use in the present invention are as follows: inorganic pigments such as selenium, selenium—tellurium, cadmium sulfide, cadmium sulfide—selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53 -95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 3 can be obtained as follows:

The charge generating material is vacuum-deposited on the electroconductive support 1, or the dispersion in which finely-divided particles of the charge generating material 3 is dispersed in an appropriate solvent, together with the binder agent when necessary, is coated on the electroconductive support 1 and dried, so that the charge generation layer 5 is formed. When necessary, the charge generation layer 5 is subjected to surface treatment by buffing and adjustment of the thickness thereof. On the thus formed charge generation layer 5, a coating solution in which at least one polyether compound and the binder agent are dissolved is coated and dried, so that the charge transport layer 4 is formed. In the charge generation layer 5, the same charge generating material as employed in the above-mentioned photoconductive layer 2*a* can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 is dispersed in an appropriate solvent together with the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the polyether compound contained in the charge transport layer 4 be in the range of 10 to 95 wt. %, more preferably in the range of 30 to 90 wt. %.

The electrophotographic photoconductor shown in FIG. 4 can be obtained as follows:

A coating solution in which the diamine compound and the binder agent are dissolved is coated on the electroconductive support 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The amount ratio of components contained in the charge generation layer and charge transport layer is the same as previously described in FIG. 3.

The electrophotographic photoconductor shown in FIG. 5 can be obtained by forming a protective layer 6 on the charge generation layer 5 as obtained in FIG. 4 by spray-coating of an appropriate resin solution. As a resin employed in the protective layer 6, any of binder agents to be described later can be used.

Specific examples of the electroconductive support 1 for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. Any insulating and adhesive resins can be employed.

Some plasticizers may be added to the abovementioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

PREPARATION EXAMPLE 1-1

[Synthesis of Diamine Compound No. 27 in TABLE 1]

42.5 g (0.2 mol) of o-tolidine was dissolved in 200 ml of methanol. To this solution, 20.4 g (0.2 mol) of acetic anhydride was added dropwise over a period of 2 hours. After the dropwise addition of the acetic anhydride, the reaction mixture was poured over 300 g of ice, so that separated crystals were filtered off.

The thus obtained crystals were dispersed in an aqueous solution of hydrochloric acid composed of 100 ml of hydrochloric acid and 1000 ml of water. This mixture was stirred at room temperature for 1 hour and was then filtered to obtain a filtrate. To the filtrate was added potassium hydroxide to make the filtrate highly basic. Crystals separated from the filtrate were filtered off, whereby N-acetyl-o-tolidine (m.p. 207°–209° C.) was obtained in a yield of 24.0 g (47%).

The infrared spectrum absorption of νc=o measured by a commercially available infrared spectrophotometer IR-700 (made by Nippon Bunko Kogyo Co., Ltd.) by using a KBr tablet was 1651 $cm^{-1}$.

To 50 ml of nitrobenzene, 7.63 g (30 mmol) of the thus obtained N-acetyl-o-tolidine, 21.8 g (100 mmol) of p-iodotoluene, 0.63 g (10 mmol) of copper powder, and 14.7 g (150 mmol) of anhydrous potassium carbonate were added. The mixture was stirred at 200° C. for 10 hours.

After this stirring with application of heat, this reaction mixture was poured into an aqueous solution of 5.6 g (100 mmol) of 96% potassium hydroxide in a mixture of 50 ml of isoamyl alcohol and 20 ml of water, and hydrolyzed at 120° C. for 8 hours.

The reaction mixture was steam distilled to remove the isoamyl alcohol and nitrobenzene therefrom and was extracted with 200 ml of toluene.

With insoluble components removed from the toluene layer by filtration, the toluene layer was washed water, dried, and concentrated. Crystals were obtained from the residue. The thus obtained crystals were column-chromatographed for purification on silica gel and eluted with a mixed solvent of toluene and n-hexane (1:2), whereby N,N,N'-tris(4-methylphenyl)-o-tolidine (m.p. 141.0°–143.0° C.) was obtained in a yield of 10.9 g (74%).

3.93 g (10 mmol) of the thus obtained N,N,N'-tris(4-methylphenyl)-o-tolidine, 4.10 g (12.5 mmol) of 1-iodopyrene, 0.19 g (3 mmol) of copper powder, and 3.92 g (40 mmol) of anhydrous potassium carbonate were added to 50 ml of nitrobenzene. This reaction mixture was stirred at 200° C. for 7 hours.

After the completion of this stirring with the application of heat, the reaction mixture was extracted with 100 ml of toluene, and the toluene layer was concentrated, whereby a yellow oil was obtained as a reaction product.

The thus obtained yellow oil was column-chromatographed for purification on silica gel and eluted with a mixed solvent of toluene and n-hexane (1:2), whereby N-(1-pyrenyl)-N,N',N'-tris(4-methylphenyl)-o-tolidine (m.p. 232.0°–233.5° C.) was obtained in a yield of 3.11 g (39%).

The results of the elemental analysis of the thus obtained compound were as follows:

| | % C | % H | % N |
|---|---|---|---|
| Found | 90.05 | 6.44 | 3.89 |
| Calculated | 89.70 | 6.20 | 4.10 |

The above calculation was based on the formula for N-(1-Pyrenyl)-N,N',N'-tris(4-methylphenyl)-o-tolidine of $C_{51}H_{42}N_2$.

Figure 6:
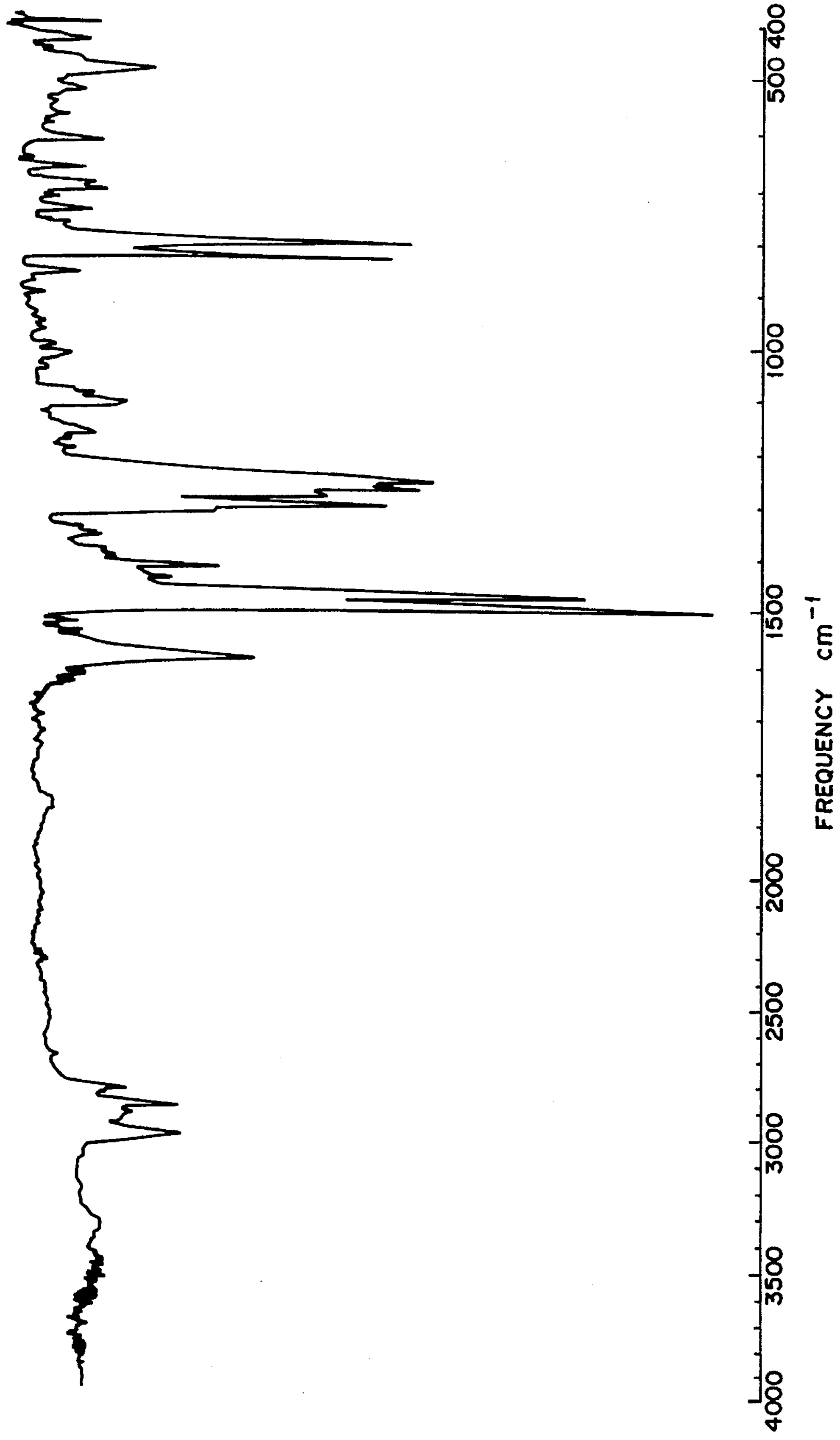
FIG. 6 as an infrared spectrum of a diamine compound, N-(1-pyrenyl)-N,N',N'-tris(4-methylphenyl)-o-tolidine, according to the present invention.

FIG. 6 shows an infrared spectrum of N-(1-pyrenyl)-N,N',N'-tris(4-methylphenyl)-o-tolidine, taken by use of a KBr tablet.

PREPARATION EXAMPLE 1-2

[Synthesis of Diamine Compound No. 28 in TABLE 1]

7.63 g (30 mmol) of N-acetyl-o-tolidine synthesized in Preparation Example 1-1, 21.8 g (100 mmol) of m-iodotoluene, 0.63 g (10 mmol) of copper powder, and 14.7 g (150 mmol) of anhydrous potassium carbonate were added to 50 ml of nitrobenzene. The mixture was stirred at 200° C. for 10 hours.

After this stirring with application of heat, this reaction mixture was poured into an aqueous solution of 5.6 g (100 mmol) of 96% potassium hydroxide in a mixture of 50 ml of isoamyl alcohol and 20 ml of water, and hydrolyzed at 120° C. for 12 hours.

The reaction mixture was steam distilled to remove the isoamyl alcohol and nitrobenzene therefrom and was extracted with 200 ml of toluene.

With insoluble components removed from the toluene layer by filtration, the toluene layer was washed water, dried, and concentrated. Crystals were obtained from the residue. The thus obtained crystals were column-chromatographed for purification on silica gel and eluted with a mixed solvent of toluene and n-hexane (1:2), whereby N,N,N'-tris(3-methylphenyl)-o-tolidine was obtained in a yield of 12.5 g (85%).

3.93 (10 mmol) of the thus obtained N,N,N'-tris(4-methylphenyl)-o-tolidine, 4.10 g (12.5 mmol) of 1-iodopyrene, 0.19 g (3 mmol) of copper powder, and 3.92 g (40 mmol) of anhydrous potassium carbonate were added to 50 ml of nitrobenzene. This reaction mixture was stirred at 200° C. for 7 hours.

After the completion of this stirring with the application of heat, the reaction mixture was extracted with 100 ml of toluene, and the toluene layer was concentrated, whereby a yellow oil was obtained as a reaction product.

The thus obtained yellow oil was column-chromatographed for purification on silica gel and eluted with a mixed solvent of toluene and n-hexane (1:2), whereby N-(1-pyrenyl)-N,N',N'-tris(3-methylphenyl)-o-tolidine (with a melting initiation point of 130.5° C.) was obtained in a yield of 2.3 g (34%).

The results of the elemental analysis of the thus obtained compound were as follows:

| | % C | % H | % N |
|---|---|---|---|
| Found | 89.80 | 6.50 | 3.80 |
| Calculated | 89.70 | 6.20 | 4.10 |

The above calculation was based on the formula for N-(1-pyrenyl)-N,N',N'-tris (3-methylphenyl)-o-tolidine of $C_{51}H_{42}N_2$.

PREPARATION EXAMPLE 1-3

[Synthesis of Diamine Compound No. 29 in TABLE 1]

7.63 g (30 mmol) of N-acetyl-o-tolidine synthesized in Preparation Example 1-1, 23.6 g (100 mmol) of p-iodoanisole, 0.63 g (10 mmol) of copper powder, and 14.7 g (150 mmol) of anhydrous potassium carbonate were added to 50 ml of nitrobenzene. The mixture was stirred at 200° C. for 10 hours.

After this stirring with application of heat, this reaction mixture was poured into an aqueous solution of 5.6 g (100 mmol) of 96% potassium hydroxide in a mixture of 50 ml of isoamyl alcohol and 20 ml of water, and hydrolyzed at 120° C. for 8 hours.

The reaction mixture was steam distilled to remove the isoamyl alcohol and nitrobenzene therefrom and was extracted with 200 ml of toluene.

With insoluble components removed from the toluene layer by filtration, the toluene layer was washed water, dried, and concentrated. Crystals were obtained from the residue. The thus obtained crystals were column-chromatographed for purification on silica gel and eluted with a mixed solvent of toluene and n-hexane (1:2), whereby N,N,N'-tris(4-methoxyphenyl)-o-tolidine (m.p. 96.0°–98.5° C.) was obtained in a yield of 8.14 g (54%).

5.30 g (10 mmol) of the thus obtained N,N,N'-tris(4-methoxyphenyl)-o-tolidine, 4.10 g (12.5 mmol) of 1-iodopyrene, 0.19 g (3 mmol) of copper powder, and 3.92 g (40 mmol) of anhydrous potassium carbonate were added to 50 ml of nitrobenzene. This reaction mixture was stirred at 200° C. for 12 hours.

After the completion of this stirring with the application of heat, the reaction mixture was extracted with 100 ml of toluene, and the toluene layer was concentrated, whereby a yellow oil was obtained as a reaction product.

The thus obtained yellow oil was column-chromatographed for purification on silica gel and eluted with a mixed solvent of toluene and n-hexane (1:5), whereby N-(1-pyrenyl)-N,N',N'-tris(4-methoxyphenyl)-o-tolidine (m.p. 175.0°–177.5° C.) was obtained in a yield of 2.6 g (36%).

The results of the elemental analysis of the thus obtained compound were as follows:

| | % C | % H | % N |
|---|---|---|---|
| Found | 84.07 | 5.88 | 3.30 |
| Calculated | 83.81 | 5.79 | 3.80 |

The above calculation was based on the formula for N-(1-pyrenyl)-N,N',N'-tris (4-methoxyphenyl)-o-tolidine of $C_{51}H_{42}N_2O_3$.

PREPARATION EXAMPLE 1-4

[Synthesis of Diamine Compound No. 30 in TABLE 1]

7.63 g (30 mmol) of N-acetyl-o-tolidine synthesized in Preparation Example 1-1, 23.6 g (100 mmol) of m-iodoanisole, 0.63 g (10 mmol) of copper powder, and 14.7 g (150 mmol) of anhydrous potassium carbonate were added to 50 ml of nitrobenzene. The mixture was stirred at 200° C. for 10 hours.

After this stirring with application of heat, this reaction mixture was poured into an aqueous solution of 5.6 g (100 mmol) of 96% potassium hydroxide in a mixture of 50 ml of isoamyl alcohol and 20 ml of water, and hydrolyzed at 120° C. for 8 hours.

The reaction mixture was steam distilled to remove the isoamyl alcohol and nitrobenzene therefrom and was extracted with 200 ml of toluene.

With insoluble components removed from the toluene layer by filtration, the toluene layer was washed water, dried, and concentrated. Crystals were obtained from the residue.

The thus obtained crystals were column-chromatographed for purification on silica gel and eluted with a mixed solvent of toluene and n-hexane (1:3), whereby N,N,N'-tris(3-methoxyphenyl)-o-tolidine was obtained in a yield of 11.5 g (79%).

5.30 g (10 mmol) of the thus obtained N,N,N'-tris(3-methoxyphenyl)-o-tolidine, 4.10 g (12.5 mmol) of 1-iodopyrene, 0.19 g (3 mmol) of copper powder, and 3.92 g (40 mmol) of anhydrous potassium carbonate were added to 50 ml of nitrobenzene. This reaction mixture was stirred at 200° C. for 10 hours.

After the completion of this stirring with the application of heat, the reaction mixture was extracted with 100 ml of toluene, and the toluene layer was concentrated, whereby a yellow oil was obtained as a reaction product.

The thus obtained yellow oil was column-chromatographed for purification on silica gel and eluted with a mixed solvent of toluene and n-hexane (1:5), whereby N-(1-pyrenyl)-N,N',N'-tris(3-methoxyphenyl)-o-tolidine (m.p. 308.0°–310.0° C.) was obtained in a yield of 4.5 g (61%).

The results of the elemental analysis of the thus obtained compound were as follows:

| | % C | % H | % N |
|---|---|---|---|
| Found | 83.46 | 5.61 | 4.18 |
| Calculated | 83.81 | 5.79 | 3.80 |

The above calculation was based on the formula for N-(1-pyrenyl)-N,N',N'-tris(3-methoxyphenyl)-o-tolidine of $C_{51}H_{42}N_2O_3$.

PREPARATION EXAMPLE 1-5

[Synthesis of Diamine Compound No. 6 in TABLE 1]

5.0 g (16 mmol) of N-(m-tolyl)-1-aminopyrene, 5.3 g (16 mmol) of 4-nitro-4'-iodobiphenyl, 1.03 g (16 mmol) of copper powder, and 6.63 g (48 mmol) of anhydrous potassium carbonate were added to 50 ml of nitrobenzene. The mixture was stirred at 200° C. for 10 hours.

After this stirring with application of heat, this reaction mixture was extracted with 100 ml of toluene. The toluene layer was concentrated, whereby red crystals were obtained from the residue.

The thus obtained red crystals were column-chromatographed for purification on silica gel and eluted with a mixed solvent of toluene and n-hexane (1:2), whereby 4'-nitro-N-(m-tolyl)-N-(1-pyrenyl)-4-biphenylamine was obtained in a yield of 5.66 g (54%).

5.04 g (10 mmol) of the thus obtained 4'-nitro-N-(m-tolyl)-N-(1-pyrenyl)-4-biphenylylamine was dissolved in 150 ml of tetrahydrofuran, and 2 g of 5% palladium carbon (with a water-content of 51 wt. %) was added thereto in a hydrogenation apparatus. The nitro group of the 4'-nitro-N-(m-tolyl)-N-(1-pyrenyl)-4-biphenylylamine was reduced at room temperature by the hydrogenation apparatus.

After the completion of the reduction reaction, the palladium carbon was removed from the reaction mixture by filtration, and the terahydrofuran was distilled, whereby N-(m-tolyl)-N-(1-pyrenyl)-[1,1'-biphenyl]-4,4'-diamine was obtained in the form of crystals.

The thus obtained N-(m-tolyl)-N-(1-pyrenyl)-[1,1'-biphenyl]-4,4'-diamine, 4.8 g (22 mmol) of m-iodotoluene, 0.3 g (5 mmol) of copper powder, 4.2 g (30 mmol) of anhydrous potassium carbonate were added to 50 ml of nitrobenzene. This reaction mixture was stirred at 190° C. for 19 hours.

After the completion of this stirring with the application of heat, the reaction mixture was extracted with 100 ml of toluene, and the toluene layer was concentrated, whereby a red oil was obtained as a reaction product.

The thus obtained red oil was column-chromatographed for purification on silica gel and eluted with a mixed solvent of toluene and n-hexane (1:3), whereby N-(1-pyrenyl)-N,N',N'-tris(3-methylphenyl)benzidine (Diamine Compound No. 6) (with a melting-initiation point of 130° C.) was obtained in a yield of 2.0 g (31%).

The results of the elemental analysis of the thus obtained compound were as follows:

| | % C | % H | % N |
|---|---|---|---|
| Found | 89.83 | 5.93 | 4.06 |
| Calculated | 89.87 | 5.85 | 4.28 |

The above calculation was based on the formula for N-(1-pyrenyl)-N,N',N'-tris (3-methylphenyl) benzidine of $C_{49}H_{38}N_2$.

PREPARATION EXAMPLE 1-6

[Synthesis of Diamine Compound No. 7 in TABLE 1]

2.71 g (5.2 mmol) of 4'-nitro-N-(4-methoxyphenyl)-N-(1-pyrenyl)-4-biphenylylamine synthesized in a similar manner to that in Preparation Example 1-5 was dissolved in 150 ml of tetrahydrofuran, and 2 g of 5% palladium carbon (with a water-content of 51 wt. %) was added thereto in a hydrogenation apparatus. The nitro group of the 4'-nitro-N-(4-methoxyphenyl)-N-(1-pyrenyl)-4-biphenylylamine was reduced at room temperature by the hydrogenation apparatus.

After the completion of the reduction reaction, the palladium carbon was removed from the reaction mixture by filtration, and the terahydrofuran was distilled, whereby N-(4-methoxyphenyl)-N-(1-pyrenyl)-[1,1'-biphenyl]-4,4'-diamine was obtained in the form of crystals.

The thus obtained N-(4-methoxyphenyl)-N-(1-pyrenyl)-[1,1'-biphenyl]-4,4'-diamine, 2.7 g (11 mmol) of p-iodoanisole, 0.3 g (5 mmol) of copper powder, 2.2 g (16 mmol) of anhydrous potassium carbonate were added to 50 ml of nitrobenzene. This reaction mixture was stirred at 190° C. for 18 hours.

After the completion of this stirring with the application of heat, the reaction mixture was extracted with 100 ml of toluene, and the toluene layer was concentrated, whereby a red oil was obtained as a reaction product.

The thus obtained red oil was column-chromatographed for purification on silica gel and eluted with a mixed solvent of dioxane and n-hexane (1:5), whereby N-(1-pyrenyl)-N,N',N'-tris(4-methoxyphenyl)benzidine (m.p. 211.0° to 213.0° C.) was obtained in a yield of 1.2 g (33%).

The results of the elemental analysis of the thus obtained compound were as follows:

| | % C | % H | % N |
|---|---|---|---|
| Found | 84.07 | 5.53 | 3.72 |
| Calculated | 83.73 | 5.45 | 3.99 |

The above calculation was based on the formula for N-(1-pyrenyl)-N,N',N'-tris(4-methoxyphenyl)benzidine of $C_{49}H_{38}N_2O_3$.

PREPARATION EXAMPLE 1-7

[Synthesis of Diamine Compound No. 60 in TABLE 1]

By subjecting 4'-iodo-N-(p-tolyl)-N-(1-pyrenyl)-4-biphenlyamine and 3-methylbiphenylylamine to the same Ullmann reaction as in Preparation Example 1-6, whereby N-(1-Pyrenyl)-N-(p-tolyl)-N'-phenyl-N'-(m-tolyl)benzidine (m.p. 172.0°–173.0° C.) was obtained.

The results of the elemental analysis of the thus obtained compound were as follows:

| | % C | % H | % N |
|---|---|---|---|
| Found | 89.46 | 5.32 | 4.32 |
| Calculated | 89.96 | 5.66 | 4.37 |

The above calculation was based on the formula for N-(1-Pyrenyl)-N-(p-tolyl)-N'-phenyl-N'-(m-tolyl)benzidine of $C_{48}H_{36}N_2$.

PREPARATION EXAMPLE 1-8

[Synthesis of Diamine Compound No. 61 in TABLE 1]

3,3',5,5'-tetramethylbenzidine was monoacetylated by a conventional method, and the thus obtained monoacetylated compound and p-iodotoluene to the Ullmann reaction, whereby N,N,N'-tris(4-methylphenyl)-N'-acetyl-3,3',5,5'-tetramethylbenzidine was obtained.

The thus obtained N,N,N'-tris(4-methylphenyl)-N'-acetyl-3,3',5,5'-tetramethylbenzidine was hydrolyzed, and the hydrolyzed product and 1-iodo-pyrene were subjected to the same Ullmann reaction as in Preparation Example 1-6, whereby N,N,N'-tris(4-methylphenyl)-N'-(1-pyrenyl)-3,3',5,5'-tetramethylbenzidine (m.p. 198.0°–199.0° C.) was obtained.

The results of the elemental analysis of the thus obtained compound were as follows:

| | % C | % H | % N |
|---|---|---|---|
| Found | 89.14 | 6.74 | 3.96 |
| Calculated | 89.54 | 6.52 | 3.94 |

The above calculation was based on the formula for N,N,N'-tris(4-methylphenyl)-N'-(1-pyrenyl)-3,3',5,5'-tetramethylbenzidine of $C_{53}H_{46}N_2$.

EXAMPLE 2-1

76 parts by weight of Diane Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer with a thickness of about 1 μm was formed on the aluminum-deposited polyester film.

2 parts by weight of diamine compound No. 6 in TABLE 1, 2 parts by weight of polycarbonate resin (Trademark "Panlite K-1300" made by Teijin Limited.) and 16 parts by weight of tetrahydrofuran were mixed to form a solution.

This solution was coated on the above formed charge generation layer by a doctor blade and then dried at 80° C. for 2 minutes and then at 120° C. for 5 minutes, so that a charge transport layer with a thickness of about 20 μm was formed on the charge generation layer. Thus a two-layered type electrophotographic photoconductor No. 1 according to the present invention was prepared.

EXAMPLES 2-2 to 2-23

The procedure for preparation of the two-layered type electrophotographic photoconductor No. 1 in Example 2-1 was repeated except that Diane Blue serving as a charge generating material and the diamine compound No. 6 serving as a charge transporting material employed in Example 2-1 were replaced by the respective charge generating materials and charge transporting materials listed in the following TABLE 2, whereby two-layered type electrophotographic photoconductors No. 2 to No. 23 according to the present invention were prepared.

TABLE 2
| Example No. | Charge Generating Material | Charge Transporting Material (Diamine Derivative) |
| --- | --- | --- |
| 1 | 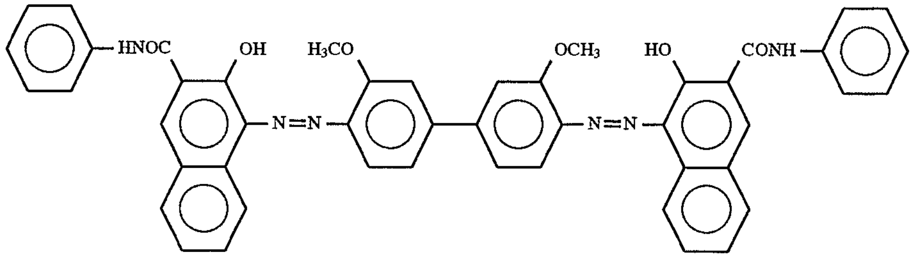 | Compound No. 6 |
| 2 | 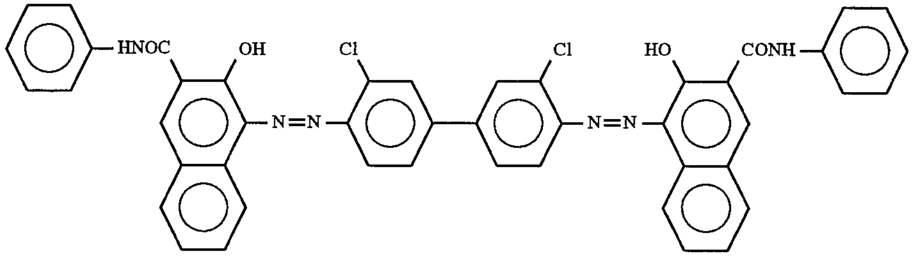 | Compound No. 6 |
| 3 | 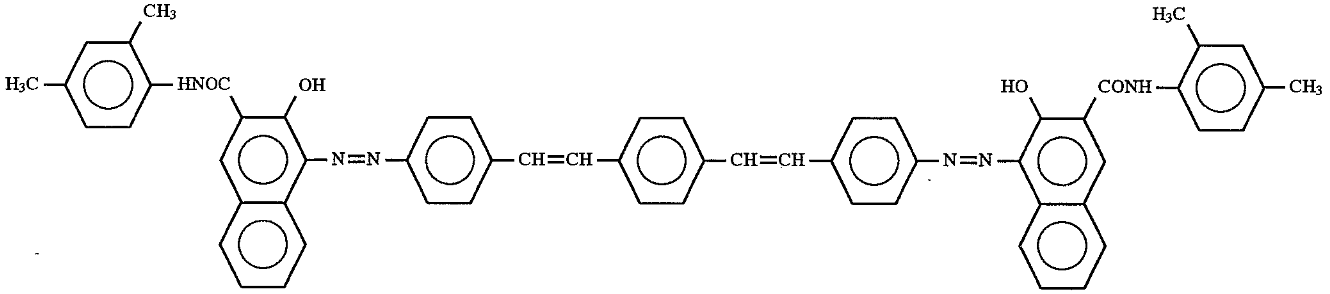 (hereinafter referred to as P-1.) | Compound No. 6 |

TABLE 2-continued
| | | |
|---|---|---|
| 4 | 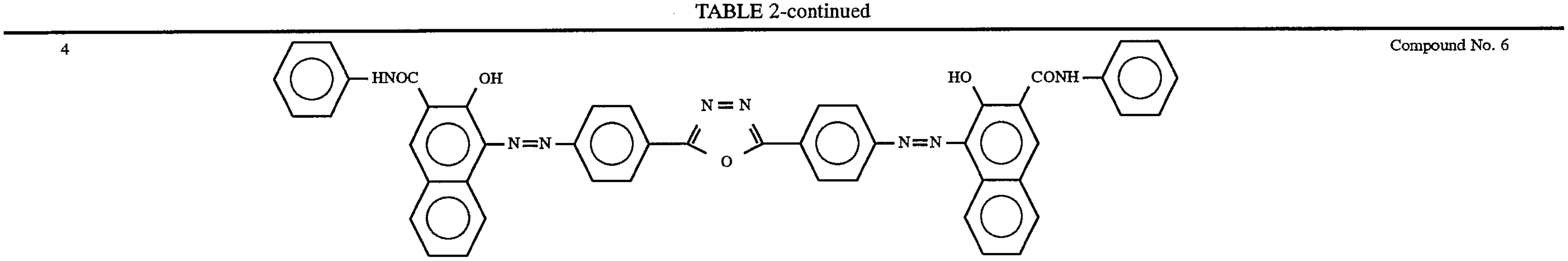 | Compound No. 6 |
| 5 | 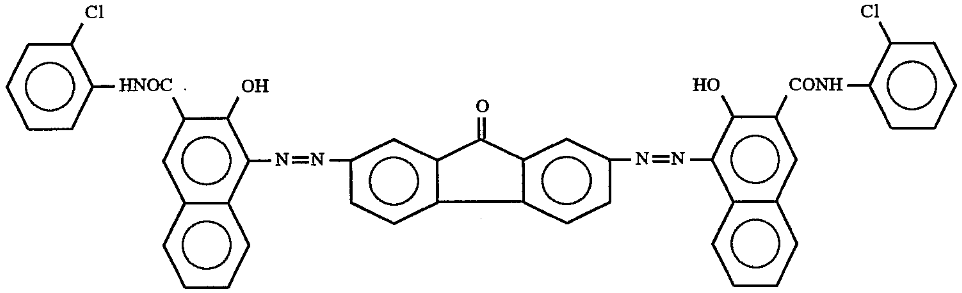<br>(hereinafter referred to as P-2.) | Compound No. 6 |
| 6 | 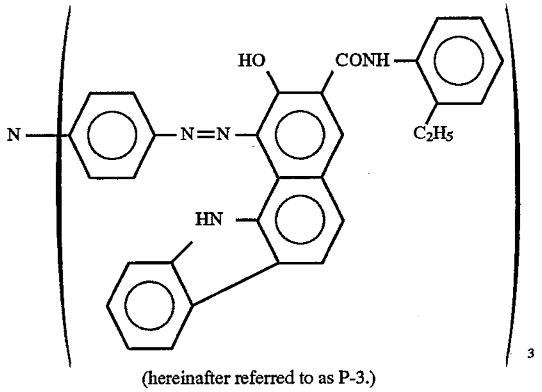<br>(hereinafter referred to as P-3.) | Compound No. 6 |
| 7 | β-type Copper Phthalocyanine | Compound No. 6 |

TABLE 2-continued
| | | |
|---|---|---|
| 8 | 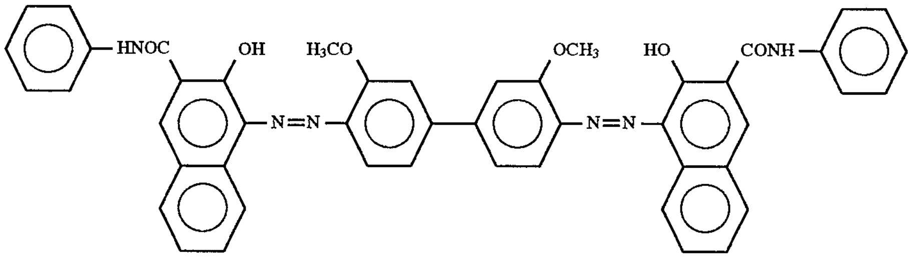 | Compound No. 7 |
| 9 | 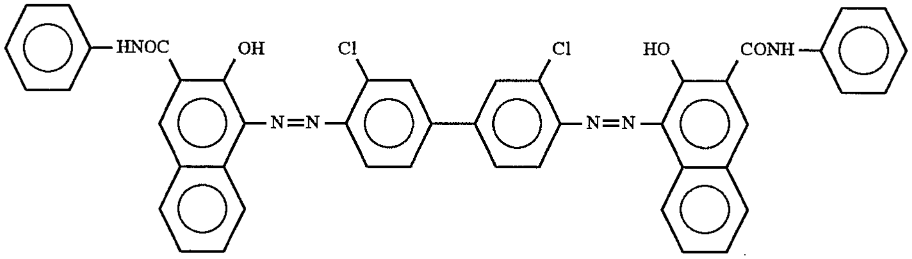 | Compound No. 7 |
| 10 | P-1 | Compound No. 7 |
| 11 | P-2 | Compound No. 7 |
| 12 | P-3 | Compound No. 7 |
| 13 | P-1 | Compound No. 27 |
| Example No. | Charge Generating Material | Charge Transporting Material (Diamine Compound No.) |
|---|---|---|
| 14 | P-2 | 27 |
| 15 | P-3 | 27 |
| 16 | P-1 | 28 |
| 17 | P-2 | 28 |
| 18 | P-3 | 28 |
| 19 | P-1 | 29 |
| 20 | P-2 | 29 |
| 21 | P-3 | 29 |
| 22 | P-2 | 60 |
| 23 | P-2 | 61 |

EXAMPLE 2-24

Selenium was vacuum-deposited on an aluminum plate with a thickness of about 300 μm, so that a charge generation layer with a thickness of about 1 μm was formed on the aluminum plate.

2 parts by weight of diamine compound No. 6 in TABLE 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer with a thickness of about 10 μm was formed on the charge generation layer. Thus a two-layered type electrophotographic photoconductor No. 24 according to the present invention was prepared.

EXAMPLE 2-25

The procedure for preparation of the two-layered electrophotographic photoconductor No. 24 in Example 2-24 was repeated except that a charge generation layer with a thickness of about 0.6 μm was formed on the same aluminum plate as employed in Example 2-24 by deposition of the following perylene pigment instead of selenium, so that a two-layered electrophotographic photoconductor No. 25 according to the present invention was prepared:

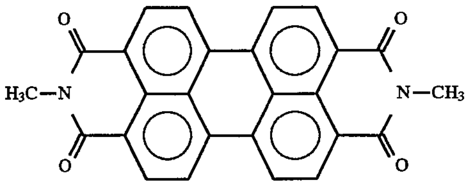

EXAMPLE 2-26

A mixture of 1 part by weight of the same Diane Blue as employed in Example 2-1 and 158 parts by weight of tetrahydrofuran was dispersed and ground in a ball mill to form a dispersion. To the thus formed dispersion, 12 parts by weight of diamine compound No. 6 in TABLE 1 and 18 parts by weight of polyester resin (Trademark "Polyester Adhesive 49000" made by Du Pont de Nemours, E.I. & Co.) were added to form a solution.

This solution was coated on an aluminum-deposited polyester film by a doctor blade, and dried at 100° C. for 30 minutes, so that a photoconductive layer with a thickness of about 16 μm was formed on the electroconductive support. Thus, an electrophotographic photoconductor No. 26 according to the present invention was prepared.

EXAMPLE 2-27

2 parts by weight of diamine compound No. 6 in TABLE 1, 2 parts by weight of polycarbonate resin (Trademark "Panlite K-1300" made by Teijin Limited.) and 16 parts by weight of tetrahydrofuran were mixed to form a solution.

This solution was coated on an aluminum surface of an aluminum-deposited polyester film by a doctor blade and then dried at 80° C. for 2 minutes and then at 120° C. for 5 minutes, so that a charge transport layer with a thickness of about 20 μm was formed on the aluminum-deposited polyester.

A mixture of 13.5 parts by weight of bisazo pigment (P-2), 5.4 parts by weight of polyvinyl butyral (Trademark "XYHL" made by Union Carbide Japan K. K.), 680 parts by weight of tetrahydrofuran and 1020 parts by weight of ethyl cellosolve was dispersed and ground in a ball mill. To this dispersion, 1700 parts by weight of additional ethyl cellosolve was added to form a solution. This solution was coated on the above formed charge transport layer by spray coating and dried at 100° C. for 10 minutes, so that a charge generation layer with a thickness of about 0.2 μm was formed on the charge transport layer.

A methanol—n-butanol based solution of a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, an electrophotographic photoconductor No. 27 according to the present invention was prepared.

Each of the thus prepared electrophotographic photoconductors No. 1 through No. 27 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E^{+bd}$ ½ (lux.sec) required to reduce the initial surface potential Vpo (V) to ½ the initial surface potential Vpo (V) was measured. The results are shown in TABLE 3.

Each of the thus fabricated electrophotographic photoconductors Nos. 1 to 27 according to the present invention was charged by use of a commercially available electrophotographic copying machine and exposed to a light image to form a corresponding latent electrostatic image thereon. The thus formed latent electrostatic image formed on each of the photoconductors was developed with a dry developer to a visible toner image. The thus formed toner image was then electrostatically transferred to a plain paper and fixed thereto. As a result, a clear transferred toner image was obtained from each of the photoconductors.

When a liquid developer was employed instead of the dry developer, a clear transferred toner image was also obtained from each of the electrophotographic photoconductors Nos. 1 to 27 of the present invention.

TABLE 3

| Photoconductor | −Vpo (V) | $E_{1/2}$ (lux · sec) |
|---|---|---|
| No. 1 | 1023 | 1.90 |
| No. 2 | 993 | 1.70 |
| No. 3 | 1192 | 1.10 |
| No. 4 | 1221 | 1.87 |
| No. 5 | 1136 | 0.93 |
| No. 6 | 984 | 0.59 |
| No. 7 | 1210 | 1.32 |
| No. 8 | 917 | 1.58 |
| No. 9 | 735 | 1.20 |
| No. 10 | 821 | 0.83 |
| No. 11 | 597 | 0.59 |
| No. 12 | 485 | 0.30 |
| No. 13 | 1197 | 1.20 |
| No. 14 | 1128 | 1.07 |
| No. 15 | 947 | 0.88 |
| No. 16 | 1311 | 1.40 |

TABLE 3-continued

| Photoconductor | −Vpo (V) | $E_{1/2}$ (lux · sec) |
|---|---|---|
| No. 17 | 1256 | 1.20 |
| No. 18 | 1100 | 0.87 |
| No. 19 | 1103 | 1.03 |
| No. 20 | 1004 | 0.91 |
| No. 21 | 971 | 0.60 |
| No. 22 | 858 | 0.72 |
| No. 23 | 1085 | 0.95 |
| No. 24 | 1251 | 2.81 |
| No. 25 | 1393 | 3.72 |
| No. 26 | −1095 | 1.70 |
| No. 27 | −1240 | 0.98 |

The electrophotographic photoconductors according to the present invention comprise a photoconductive layer comprising any of the above-mentioned specific diamine compounds serving as an organic photoconductive material, so that the resistance to heat and mechanical shocks and the photoconductive properties can be significantly improved. Furthermore, the photoconductors according to the present invention can be manufactured at low cost. Japanese Patent Application No. 5-285857 filed on Oct. 20, 1993, Japanese Patent Application No. 5-296045 filed on Nov. 1, 1993, Japanese Patent Application No. 6-109088 filed on Apr. 25, 1994, and Japanese Patent Application No. 6-109087 filed on Apr. 25, 1994 are hereby incorporated by reference.

What is claimed is:

1. A diamine compound represented by formula (I):

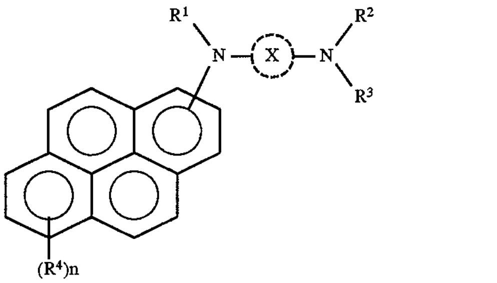

(I)

wherein $R^1$, $R^2$, and $R^3$ each is independently a substituted or unsubstituted alkyl group or aryl group not including pyrenyl; $R^4$ is hydrogen, an alkyl group or an alkoxyl group; n is an integer of 1 to 3; and

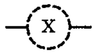

is a substituted or unsubstituted bivalent arylene group not including phenylene, phenanthrenyl and 9,10-dihydrophenanthrenyl or a bivalent heterocyclic group.

2. The diamine compound as claimed in claim 1, wherein said alkyl group represented by $R^1$, $R^2$ and $R^3$ is a straight chain or branched alkyl group having 1 to 12 carbon atoms.

3. The diamine compound as claimed in claim 1, wherein said aryl group represented by $R^1$, $R^2$ and $R^3$ is a non-fused hydrocarbon group.

4. The diamine compound as claimed in claim 1, wherein said aryl group represented by $R^1$, $R^2$ and $R^3$ is a fused polycyclic hydrocarbon group.

5. The diamine compound as claimed in claim 3, wherein said non-fused hydrocarbon group is selected from the group consisting of phenyl group, biphenylyl group, and terphenylyl group.

6. The diamine compound as claimed in claim 4, wherein said fused polycyclic hydrocarbon group has 18 or less carbon atoms which form rings therein.

7. The diamine compound as claimed in claim 6, wherein said fused polycyclic hydrocarbon group is selected from the group consisting of pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthrenyl group, anthryl group, fluoranthenyl group, acephenanthrenyl group, aceanthrenyl group, triphenylenyl group, chrysenyl group, and naphthacenyl group.

8. The diamine compound as claimed in claim 1, wherein said bivalent arylene group represented by

is a bivalent group of a substituted or unsubstituted monocyclic hydrocarbon compound.

9. The diamine compound as claimed in claim 8, wherein said monocyclic hydrocarbon compound is selected from the group consisting of diphenyl ether, polyethylene glycol diphenyl ether, diphenylthio ether, and diphenylsulfone.

10. The diamine compound as claimed in claim 1, wherein said bivalent arylene group represented by

is a bivalent group of a non-fused polycyclic hydrocarbon compound.

11. The diamine compound as claimed in claim 10, wherein said bivalent group of a non-fused polycyclic hydrocarbon compound is selected from the group consisting of biphenyl, polyphenyl, diphenyl alkane, diphenyl alkene, diphenyl alkyne, triphenyl methane, distyrylbenzene, 1,1-diphenylcyclo alkane, polyphenyl alkane, and polyphenyl alkene.

12. The diamine compound as claimed in claim 1, wherein said bivalent arylene group represented by

is a bivalent group of a fused polycyclic hydrocarbon compound.

13. The diamine compound as claimed in claim 12, wherein said fused polycyclic hydrocarbon group has 18 or less carbon atoms which form rings therein.

14. The diamine compound as claimed in claim 13, wherein said fused polycyclic hydrocarbon group is selected from the group consisting of pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, anthryl group, fluoranthenyl group, acephenanthrenyl group, aceanthrenyl group, triphenylenyl group, pyrenyl group, chrysenyl group, and naphthacenyl group.

15. The diamine compound as claimed in claim 1, wherein said bivalent arylene group represented by

is a bivalent group of a hydrocarbon ring compound.

16. The diamine compound as claimed in claim 1, wherein said bivalent heterocyclic group represented by

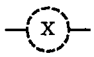

is selected from the group consisting of bivalent groups of carbazole, dibenzofuran, dibenzo-thiophene, oxadiazole, and thiadiazole.

17. A diamine compound represented by formula (Ia):

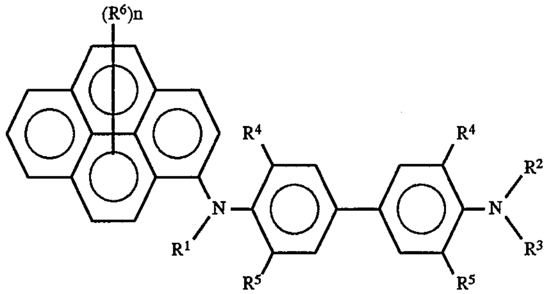

(Ia)

wherein $R^1$, $R^2$ and $R^3$ each is independently a substituted or unsubstituted alkyl group or aryl group not including pyrenyl; $R^4$ is hydrogen, a halogen atom, methoxy group or methyl group; $R^5$ is hydrogen or methyl group; $R^6$ is hydrogen, an alkyl group or an alkoxyl group; and n is an integer of 1 to 3.

18. The diamine compound as claimed in claim 17, wherein said alkyl group represented by $R^1$, $R^2$, or $R^3$ is selected from the group consisting of methyl group, ethyl group, propyl group, butyl group and benzyl group.

19. The diamine compound as claimed in claim 17, wherein said aryl group represented by $R^1$, $R^2$, or $R^3$ is selected from the group consisting of phenyl group, biphenylyl group, terphenylyl group, naphthyl group, and anthryl group.

20. The diamine compound as claimed in claim 17, wherein said alkyl group represented by $R^6$ is selected from the group consisting of methyl group, ethyl group, and butyl group.

21. The diamine compound as claimed in claim 17, wherein said alkoxyl group represented by $R^6$ is selected from the group methoxy group and ethoxy group.

* * * * *

UNITED STATES PATENT AND TRADEMARK OFFICE

CERTIFICATE OF CORRECTION

PATENT NO. : 5,631,404
DATED : MAY 20, 1997
INVENTOR(S) : MITSUTOSHI ANZAI ET AL

It is certified that error appears in the above-identified patent and that said Letters Patent is hereby corrected as shown below:

Column 17, line 43, "or" should read --of--;
line 60, "or" should read --of--.

Column 20, line 27, "washed water," should read --washed with water,--.

Column 21, line 21, "washed water," should read --washed with water,--.

Column 22, line 10, "washed water," should read --washed with water,--;
line 66 "washed water," should read --washed with water,--.

Signed and Sealed this

Thirtieth Day of June, 1998

Attest:

BRUCE LEHMAN

*Attesting Officer* *Commissioner of Patents and Trademarks*